US010557841B2

(12) United States Patent
Higuchi (10) Patent No.: US 10,557,841 B2
(45) Date of Patent: Feb. 11, 2020

(54) SENSOR CONTROL APPARATUS AND SENSOR CONTROL SYSTEM

(71) Applicant: NGK Spark Plug Co., LTD., Nagoya (JP)

(72) Inventor: Yuzo Higuchi, Komaki (JP)

(73) Assignee: NGK Spark Plug Co., LTD., Nagoya (JP)

(*) Notice: Subject to any disclaimer, the term of this patent is extended or adjusted under 35 U.S.C. 154(b) by 96 days.

(21) Appl. No.: 14/990,535

(22) Filed: Jan. 7, 2016

(65) Prior Publication Data

US 2016/0209385 A1   Jul. 21, 2016

(30) Foreign Application Priority Data

Jan. 15, 2015  (JP) .................. 2015-005908

(51) Int. Cl.
*G01N 33/00* (2006.01)
(52) U.S. Cl.
CPC ..... *G01N 33/0073* (2013.01); *G01N 33/0036* (2013.01)
(58) Field of Classification Search
CPC ............ G01N 33/0073; G01N 33/0036
USPC ....................... 73/31.05
See application file for complete search history.

(56) References Cited

U.S. PATENT DOCUMENTS

| 6,055,972 A * | 5/2000 | Fujimoto | G01N 27/4067 123/688 |
| 2010/0204928 A1* | 8/2010 | Lepsch | F02D 19/0605 702/27 |

FOREIGN PATENT DOCUMENTS

JP   2005-315757 A   11/2005

* cited by examiner

*Primary Examiner* — Justin Seo
*Assistant Examiner* — Rodney T Frank
(74) *Attorney, Agent, or Firm* — Leason Ellis LLP (57) ABSTRACT

A sensor control apparatus controls a gas sensor which measures the concentration of oxygen contained in exhaust gas. A current DA converter of the sensor control apparatus supplies a current having a current value designated by a control section (hereinafter referred to as the designated current value) to a label resistor having a resistance previously set so as to represent the characteristic of the gas sensor (hereinafter referred to as the characteristic resistance). Further, the control section of the sensor control apparatus sets the designated current value to a plurality of values in accordance with the characteristic resistance of the label resistor.

12 Claims, 3 Drawing Sheets

SENSOR CONTROL APPARATUS AND SENSOR CONTROL SYSTEM

This application claims the benefit of Japanese Patent Applications No. 2015-005908, filed Jan. 15, 2015, which is incorporated herein by reference in its entity.

FIELD OF THE INVENTION

The present invention relates to a sensor control apparatus for controlling a gas sensor, and to a sensor control system including the sensor control apparatus and the gas sensor.

BACKGROUND OF THE INVENTION

Conventionally, there has been known a gas sensor which detects the concentration of a particular gas contained in a mixed gas. However, in some cases, the characteristic of a gas sensor which represents the relation between the concentration of the particular gas contained in the gas and a concentration signal output from the gas sensor in accordance with the concentration of the particular gas (hereafter, the characteristic will be referred to as the particular-gas concentration characteristic) may vary slightly among gas sensors due to a variation involved in production of gas sensors.

According to a known technique, in view of the above, for each of a plurality of gas sensors, one of a plurality of previously set ranks is assigned to the gas sensor on the basis of its particular-gas concentration characteristic, and a label resistor having a resistance corresponding to the assigned rank is attached to the gas sensor (see, for example, Japanese Patent Application Laid-Open (kokai) No. 2005-315757). This technique makes it possible to determine the particular-gas concentration characteristic of a gas sensor to be used on the basis of the resistance of the label resistor and accurately calculate the concentration of the particular gas using the determined particular-gas concentration characteristic. Notably, the resistance of the label resistor is calculated on the basis of a voltage between opposite ends of the label resistor (hereinafter referred to as the "label resistor voltage") measured when a resistance measurement current having a current value set in advance is supplied to the label resistor.

Problem to be Solved by the Invention

The larger the number of the ranks set for a plurality of gas sensors on the basis of their particular-gas concentration characteristics, the higher the accuracy in determining the particular-gas concentration characteristic of each gas sensor on the basis of the assigned rank, and the higher the detection accuracy of the concentration of the particular gas.

However, in the case where the label resistor voltages corresponding to all the ranks set in advance are determined to fall within the voltage measurement range of a voltage measurement circuit for measuring the label resistor voltages, as the total number of the ranks increases, the voltage difference between adjacent ranks decreases, which increases the degree of difficulty in determining the rank of each gas sensor on the basis of its label resistor voltage. Therefore, there has been a problem in that when the total number of the ranks increases, it becomes difficult to improve the detection accuracy of the concentration of the particular gas.

The present invention has been accomplished in view of such a problem, and its object is to improve the accuracy in measuring the concentration of the particular gas through use of a label resistor.

SUMMARY OF THE INVENTION

Means for Solving the Problems

The present invention which was accomplished so as to achieve the above-described object is a sensor control apparatus for controlling a gas sensor which detects a concentration of a particular gas contained in a mixed gas. The sensor control apparatus comprises energization means, also referred to as an energization device, and setting means, also referred to as a setting device.

The energization means supplies a resistance measurement current having a designated current value designated in advance to a characteristic resistor which has a characteristic resistance selected from a plurality of previously set characteristic resistances so as to represent a characteristic of the gas sensor. The setting means sets the designated current value to two or more values in accordance with a magnitude of the characteristic resistance.

The sensor control apparatus of the present invention configured as described above can calculate the characteristic resistance by measuring the value of the voltage generated between opposite ends of the characteristic resistor (hereinafter referred to as the resistor voltage) at the time when the resistance measurement current having the designated current value is supplied to the characteristic resistor. As a result, the sensor control apparatus of the present invention can determine, on the basis of the calculated characteristic resistance, the rank set in advance in accordance with the characteristic of the gas sensor.

The sensor control apparatus of the present invention sets the designated current value of the resistance measurement current supplied to the characteristic resistor such that the designated current may have two or more values in accordance with the characteristic resistance. Therefore, the sensor control apparatus of the present invention can select, by means of setting, one of two or more designated current values such that the resistor voltage represented by the product of the designated current value and the characteristic resistance falls within the voltage measurement range of the voltage measurement circuit which measures the resistor voltage. Namely, the characteristic resistances corresponding to all the ranks set in advance can be classified on the basis of the designated current value which causes the resistor voltage to fall within the voltage measurement range of the voltage measurement circuit.

Therefore, for each group of the characteristic resistances classified on the basis of the designated current value, the designated current value is determined such that the resistor voltage falls within the voltage measurement range of the voltage measurement circuit. As a result, the number of the ranks which fall within the voltage measurement range of the voltage measurement circuit can be decreased. Therefore, it is possible to prevent the difference in resistor voltage between adjacent ranks from decreasing with an increase in the total number of the ranks.

As a result, the sensor control apparatus of the present invention can increase the number of the ranks set in accordance the characteristic of the gas sensor, whereby the accuracy in measuring the concentration of the particular gas through use of the characteristic resistor can be improved.

The sensor control apparatus of the present invention preferably comprises voltage measurement means, also referred to as a voltage measurement device, for measuring a resistor voltage which is a voltage between opposite ends of the characteristic resistor at the time when the resistance measurement current flows through the characteristic resistor, wherein a first current value and a second current value smaller than the first current value are set as the designated current value. In the sensor control apparatus of the present invention, the setting means preferably sets the designated current value to change from the first current value to the second current value when the resistor voltage measured when the resistance measurement current having the first current value flows through the characteristic resistor is greater than a current changeover judgment value set in advance.

As a result, the sensor control apparatus of the present invention can classify the characteristic resistors into a group of characteristic resistors to which the current having the first current value is supplied and a group of characteristic resistors to which is supplied the current having the second current value by a simple method of judging whether or not the resistor voltage is greater than the current changeover judgment value.

In the sensor control apparatus of the present invention, the setting means preferably sets the designated current value to a plurality of values by increasing the designated current value in accordance with a current increasing procedure set in advance, and the sensor control apparatus preferably comprises voltage measurement means and current value obtainment means, also referred to as a current value obtainment device.

The voltage measurement means measures a resistor voltage which is a voltage between opposite ends of the characteristic resistor at the time when the resistance measurement current flows through the characteristic resistor. The current value obtainment means obtains the designated current value when the resistor voltage measured by the voltage measurement means reaches a measurement end judgment value set in advance.

As a result, the sensor control apparatus of the present invention can calculate the characteristic resistance on the basis of the value obtained by dividing the measurement end judgment value by the designated current value obtained by the current value obtainment means. In the sensor control apparatus of the present invention, the designated current value used for calculation of the characteristic resistance differs among the ranks set on the basis of the characteristic resistance. Therefore, only one characteristic resistance is contained in each of the characteristic resistance groups into which the characteristic resistances are classified on the basis of the designated current value. Namely, for each of the characteristic resistance groups into which the characteristic resistances are classified on the basis of the designated current value, there exists only one resistor voltage which falls within the voltage measurement range of the voltage measurement circuit. Accordingly, it is possible to prevent occurrence of a situation in which as the total number of the ranks increases, the voltage difference between ranks adjacent to each other within the voltage measurement range of the voltage measurement circuit decreases. This is because, in each of the characteristic resistance groups into which the characteristic resistances are classified on the basis of the designated current value, no adjacent rank is present.

As a result, the sensor control apparatus of the present invention can increase the number of the ranks set in accordance the characteristic of the gas sensor, whereby the accuracy in measuring the concentration of the particular gas through use of the characteristic resistor can be improved.

In the sensor control apparatus of the present invention, in the case where it comprises a current source which supplies to the gas sensor an operation control current for controlling the operation of the gas sensor, the energization means preferably supplies the resistance measurement current to the characteristic resistor by using the current source.

As a result, the sensor control apparatus of the present invention is not required to have an additional current source for supplying the resistance measurement current to the characteristic resistor, whereby the configuration of the sensor control apparatus can be simplified.

A sensor control system of the present invention preferably comprises a gas sensor which detects a concentration of a particular gas contained in a mixed gas; and a sensor control apparatus of the present invention.

Since the sensor control system of the present invention configured as described above includes the sensor control apparatus of the present invention, the sensor control system yields the same effects as those of the sensor control apparatus of the present invention.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

First Embodiment

A first embodiment of the present invention will now be described with reference to the drawings.

A gas detection system 1 of the embodiment to which the present invention is applied is used to measure the concentration of a particular gas (e.g., oxygen in the present embodiment) contained in a mixed gas (e.g., exhaust gas discharged from an internal combustion engine in the present embodiment).

Figure 1:
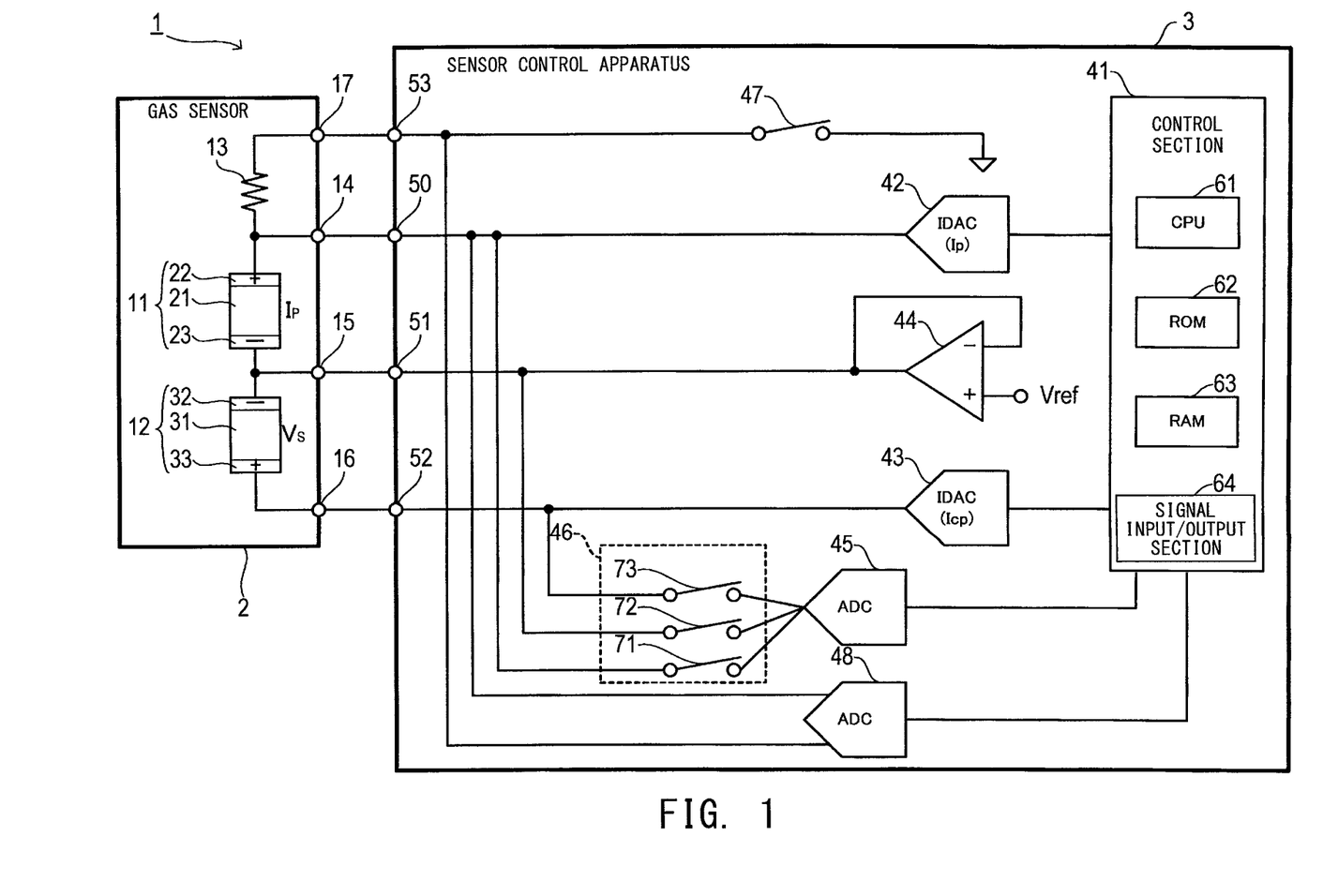
FIG. 1 is a circuit diagram showing the configuration of a gas detection system 1.

As shown in FIG. 1, the gas detection system 1 includes a gas sensor 2 and a sensor control apparatus 3.

The gas sensor 2 is disposed on an exhaust pipe of the internal combustion engine and measures the concentration of oxygen contained in the exhaust gas. The gas sensor 2 includes a pump cell 11, an electromotive force cell 12, a label resistor 13, and terminals 14, 15, 16, and 17.

The pump cell 11 has an oxygen-ion-conductive solid electrolyte member 21 formed of partially stabilized zirconia ($ZrO_2$), and a pair of porous electrodes 22 and 23 mainly formed of platinum. The porous electrodes 22 and 23 are disposed on the front surface and back surface, respectively, of the oxygen-ion-conductive solid electrolyte member 21.

The electromotive force cell 12 has an oxygen-ion-conductive solid electrolyte member 31 formed of partially stabilized zirconia ($ZrO_2$), and a pair of porous electrodes 32 and 33 mainly formed of platinum. The porous electrodes 32 and 33 are disposed on the front surface and back surface, respectively, of the oxygen-ion-conductive solid electrolyte member 31.

The gas sensor 2 has a measurement chamber (not shown) between the pump cell 11 and the electromotive force cell 12. The exhaust gas is introduced into the measurement chamber through a porous diffusion layer (not shown).

The porous electrode 23 of the pump cell 11 which faces the measurement chamber and the porous electrode 32 of the electromotive force cell 12 which faces the measurement chamber are electrically connected to each other and connected to the terminal 15. The porous electrode 22 of the pump cell 11 is connected to the terminal 14, and the porous electrode 33 of the electromotive force cell 12 is connected to the terminal 16.

The electromotive force cell 12 generates, between the porous electrode 32 and the porous electrode 33, an electromotive force corresponding to the concentration of oxygen contained in the exhaust gas within the measurement chamber. In the following description, the voltage between the porous electrode 32 and the porous electrode 33 will be referred to as the detection voltage Vs.

The label resistor 13 shows, by means of its resistance, a rank set in advance in accordance with the particular-gas concentration characteristic of the gas sensor 2 (for example, 20 ranks are set in the present embodiment). The particular-gas concentration characteristic is a characteristic which represents the relation between the concentration of the particular gas contained in the mixed gas and a concentration signal output from the gas sensor 2 in accordance with the concentration of the particular gas. Notably, the particular-gas concentration characteristic may vary among gas sensors 2 due to a variation involved in production of gas sensors 2. One end of the label resistor 13 is connected to the terminal 14, and the other end of the label resistor 13 is connected to the terminal 17.

The sensor control apparatus 3 includes a control section 41, current DA converters 42 and 43, an operational amplifier 44, an AD converter 45, a multiplexer 46, a switch 47, an AD converter 48, and terminals 50, 51, 52, and 53.

The control section 41 is composed of mainly a microcomputer which includes a CPU 61, a ROM 62, a RAM 63, a signal input/output section 64, etc. The control section 41 is configured to send and receive data, through a communication line (not shown), to and from an electronic control apparatus (not shown) which controls the internal combustion engine of a vehicle. In the following description, this electronic control apparatus will be referred to as the onboard ECU (Electronic Control Unit).

Each of the current DA converters 42 and 43 outputs a current having a current value represented by digital data input thereto.

Digital data which represent the current value of pump current Ip (which will be described later) are input to the current DA converter 42 from the control section 41, whereby the current DA converter 42 outputs the pump current Ip from its output terminal. The output terminal of the current DA converter 42 is connected to the terminal 50. The terminal 50 is connected to the terminal 14 of the gas sensor 2.

Digital data which represent the current value of minute current Icp (which will be described later) are input to the current DA converter 43 from the control section 41, whereby the current DA converter 43 outputs the minute current Icp from its output terminal. The output terminal of the current DA converter 43 is connected to the terminal 52. The terminal 52 is connected to the terminal 16 of the gas sensor 2.

A reference voltage Vref (2.5 V in the present embodiment) is applied to the non-inverting input terminal of the operational amplifier 44, and the inverting input terminal of the operational amplifier 44 is connected to the output terminal thereof. As a result, the operational amplifier 44 functions as a buffer and outputs the reference voltage Vref from the output terminal. The output terminal of the operational amplifier 44 is connected to the terminal 51. The terminal 51 is connected to the terminal 15 of the gas sensor 2.

The AD converter 45 converts the voltage value of an analog signal input thereto to digital data, and outputs the digital data to the control section 41.

The multiplexer 46 includes switches 71, 72, and 73. The switches 71, 72, and 73 are respectively provided on electrical paths extending from the terminals 50, 51, and 52 to the AD converter 45. Each of the switches 71, 72, and 73 operates to enter an on state in which the corresponding terminal 50, 51, or 52 is electrically connected to the AD converter 45 or an off state in which the corresponding terminal 50, 51, or 52 is electrically isolated from the AD converter 45.

In response to a multiplexer state instruction from the control section 41, the multiplexer 46 drives each of the switches 71, 72, and 73 such that each of the switches 71, 72, and 73 enters the on state or the off state. As a result, the AD converter 45 can convert the voltage values of the analog signals input from the terminals 50, 51, and 52 to digital data and output the digital data to the control section 41.

One end of the switch 47 is connected to the terminal 53, and the other end of the switch 47 is grounded. In response to a switch state instruction from the control section 41, the switch 47 operates to enter an on state in which the terminal 53 is grounded or an off state in which the terminal 53 is not grounded.

The AD converter 48 converts the voltage values of analog signals input from the terminals 50 and 53 to digital data, and outputs the digital data to the control section 41.

The sensor control apparatus 3 configured as described above executes processing of supplying the minute current Icp having a fixed current value such that the minute current Icp flows from the porous electrode 33 of the electromotive force cell 12 toward the porous electrode 32 thereof. As a result, the electromotive force cell 12 pumps oxygen out of the measurement chamber toward the side where the porous electrode 33 is provided. As a result, oxygen is accumulated at an approximately constant concentration in the porous electrode 33 and a reference oxygen chamber (not shown) formed therearound. The oxygen concentration within the reference oxygen chamber serves as a reference oxygen concentration when the gas sensor 2 measures the oxygen concentration of the exhaust gas.

The sensor control apparatus 3 also executes processing of controlling the pump current Ip flowing between the porous electrode 22 and the porous electrode 23 such that the detection voltage Vs of the electromotive force cell 12 becomes equal to a predetermined reference value (e.g., about 450 mV) in a state in which the constant minute current Icp is supplied to the electromotive force cell 12. As a result, the pump cell 11 pumps out oxygen contained in the exhaust gas within the measurement chamber or pumps oxygen into the measurement chamber. Namely, the control section 41 adjusts the oxygen concentration within the measurement chamber through use of the pump cell 11 such that the detection voltage Vs of the electromotive force cell 12 becomes 450 mV.

The current value and current direction of the pump current Ip change in accordance with the oxygen concentration of the exhaust gas. Therefore, the oxygen concentration of the exhaust gas can be calculated on the basis of the pump current Ip.

Also, the control section 41 of the sensor control apparatus 3 executes label resistor measurement processing.

Here, the steps of the label resistor measurement processing will be described. This label resistor measurement processing is started immediately after the startup of the sensor control apparatus 3.

Figure 2:
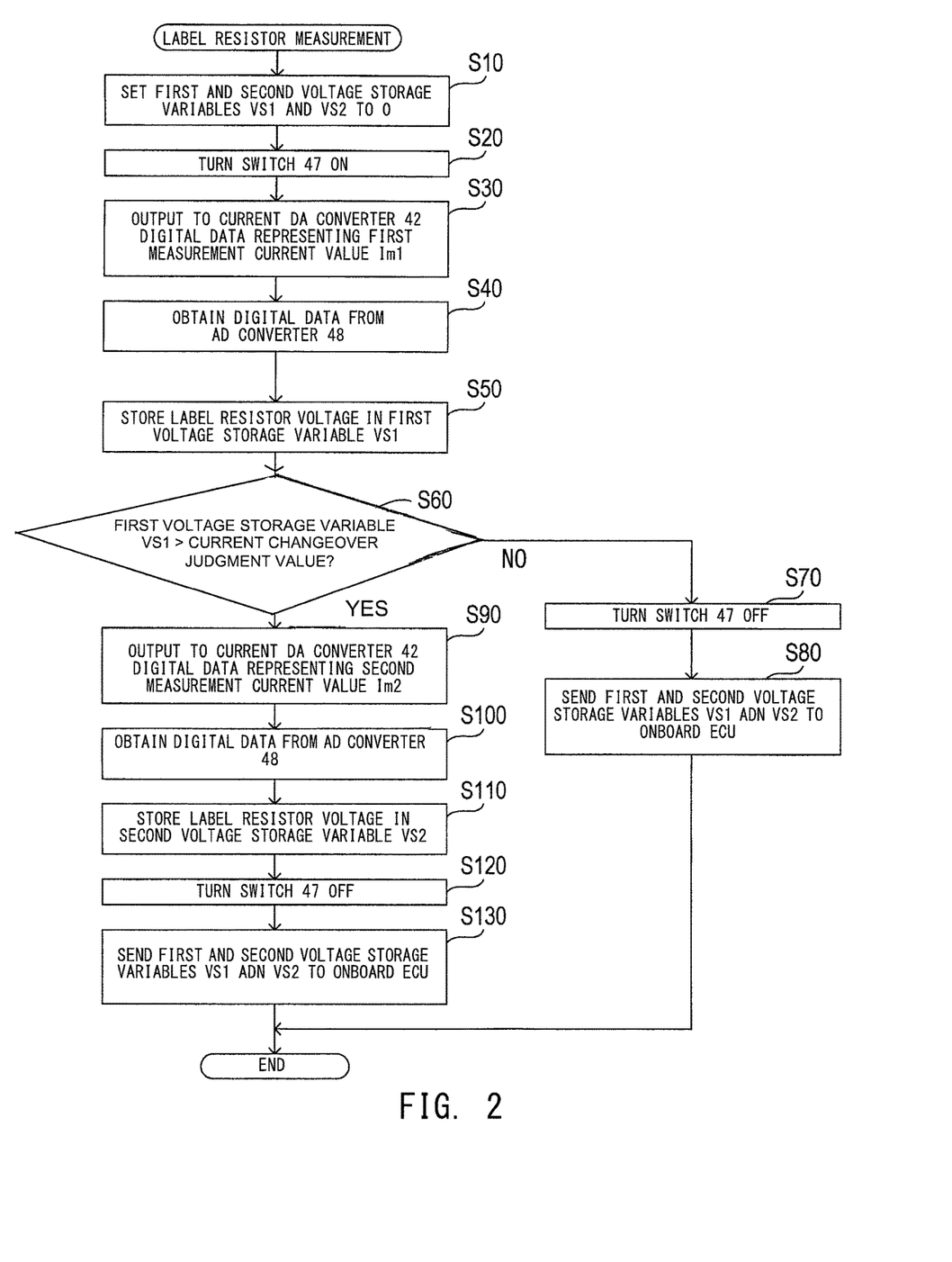
FIG. 2 is a flowchart showing label resistor measurement processing of a first embodiment.

When this label resistor measurement processing is executed, as shown in FIG. 2, in S10, the CPU 61 of the control section 41 first sets the values of a first voltage storage variable VS1 and a second voltage storage variable VS2 provided in the RAM 63 of the control section 41 to 0.

Subsequently, in S20, the CPU 61 outputs to the switch 47 a switch state instruction which instructs the switch 47 to enter the on state. As a result, the switch 47 operates to enter the on state.

Further, in S30, the CPU 61 outputs to the current DA converter 42 digital data which represent a first measurement current value Im1 (2 mA in the present embodiment) set in advance. As a result, the current DA converter 42 outputs a current having the first measurement current value Im1.

After that, in S40, the CPU 61 obtains digital data representing the voltages of the terminals 50 and 53 from the AD converter 48.

Also, in S50, the CPU 61 calculates the voltages of the terminals 50 and 53 on the basis of the digital data obtained from the AD converter 48, subtracts the voltage of the terminal 53 from the voltage of the terminal 50, and stores the resultant value in the first voltage storage variable VS1 as a label resistor voltage.

Subsequently, in S60, the CPU 61 judges whether or not the value stored in the first voltage storage variable VS1 is greater than a current changeover judgment value (a value corresponding to 1 V in the present embodiment) set in advance. In the case where the value stored in the first voltage storage variable VS1 is equal to or less than the current changeover judgment value (S60: NO), in S70, the CPU 61 outputs to the switch 47 a switch state instruction which instructs the switch 47 to enter the off state. As a result, the switch 47 operates to enter the off state. Further, in S80, the CPU 61 sends to the onboard ECU digital data which represent the value stored in the first voltage storage variable VS1 and the value stored in the second voltage storage variable VS2, and ends the label resistor measurement processing.

Meanwhile, in the case where the value stored in the first voltage storage variable VS1 is greater than the current changeover judgment value (S60: YES), in S90, the CPU 61 outputs to the current DA converter 42 digital data which represent a second measurement current value Im2 (0.2 mA in the present embodiment) set in advance to be smaller than the first measurement current value Im1. As a result, the current DA converter 42 outputs a current having the second measurement current value Im2.

After that, in S100, the CPU 61 obtains digital data representing the voltages of the terminals 50 and 53 from the AD converter 48.

Also, in S110, the CPU 61 calculates the voltages of the terminals 50 and 53 on the basis of the digital data obtained from the AD converter 48, subtracts the voltage of the terminal 53 from the voltage of the terminal 50, and stores the resultant voltage value in the second voltage storage variable VS2 as a label resistor voltage.

Next, in S120, the CPU 61 outputs to the switch 47 a switch state instruction which instructs the switch 47 to enter the off state. As a result, the switch 47 operates to enter the off state. Further, in S130, the CPU 61 sends to the onboard ECU digital data which represent the value stored in the first voltage storage variable VS1 and the value stored in the second voltage storage variable VS2, and ends the label resistor measurement processing.

The sensor control apparatus 3 configured as described above controls the gas sensor 2 which measures the concentration of oxygen contained in the exhaust gas.

The current DA converter 42 of the sensor control apparatus 3 supplies a current (hereinafter referred to as the resistance measurement current) having a current value designated by the control section 41 (hereinafter referred to as the designated current value) to the label resistor 13 having a resistance set in advance to indicate the characteristic of the gas sensor 2 (hereinafter referred to as the characteristic resistance). Further, the control section 41 of the sensor control apparatus 3 sets the designated current value to either of two different values in accordance with the magnitude of the characteristic resistance of the label resistor 13 (S30, S60, S90).

As described above, the sensor control apparatus 3 can calculate the characteristic resistance by measuring the label resistor voltage generated between the opposite ends of the label resistor 13 when the resistance measurement current having the designated current value is supplied to the label resistor 13. Thus, the sensor control apparatus 3 can determine, on the basis of the calculated characteristic resistance, the rank set in advance in accordance with the characteristic of the gas sensor 2.

The sensor control apparatus 3 sets the designated current value of the resistance measurement current supplied to the label resistor 13 to either of two different values in accordance with the magnitude of the characteristic resistance. Therefore, the sensor control apparatus 3 can set the designated current value to one of two designated current values such that the label resistor voltage represented by the product of the designated current value and the characteristic resistance falls within the voltage measurement range of the AD converter 48 which measures the label resistor voltage. Namely, the characteristic resistances corresponding to all the ranks set in advance can be classified on the basis of the designated current value which causes the label resistor voltage of each gas sensor to fall within the voltage measurement range of the AD converter 48.

Therefore, for each of the characteristic resistance groups into which all the characteristic resistances are classified on the basis of the designated current value, the designated current value is determined such that the label resistor voltage of each gas sensor falls within the voltage measurement range of the AD converter 48. As a result, the number of the ranks which fall within the voltage measurement range of the AD converter 48 can be decreased. Therefore, it is possible to prevent the difference in label resistor voltage between adjacent ranks from decreasing with an increase in the total number of the ranks.

As a result, the sensor control apparatus 3 can increase the number of the ranks set in accordance the characteristic of the gas sensor 2, whereby the accuracy in measuring the oxygen concentration through use of the label resistor 13 can be improved.

Also, the sensor control apparatus 3 includes the AD converter 48 which measures the label resistor voltage which is the voltage between the opposite ends of the label resistor 13 at the time when the resistance measurement current flows through the label resistor 13, and the first measurement current value Im1 and the second measurement current value Im2 smaller than the first measurement current value Im1 are set as the designated current value. Further, in the sensor control apparatus 3, the control section 41 switches the designated current value from the first measurement current value Im1 to the second measurement current value Im2 (S60, S90) in the case where the label resistor voltage when the resistance measurement current having the first measurement current value Im1 flows is greater than the current changeover judgment value set in advance.

As a result, the sensor control apparatus 3 can classify the characteristic resistors into a group of characteristic resistors to which the current having the first measurement current value Im1 is supplied and a group of characteristic resistors to which is supplied the current having the second measurement current value Im2 by a simple method of judging whether or not the label resistor voltage is greater than the current changeover judgment value.

Also, the current DA converter 42 is a current source for supplying to the gas sensor 2 the pump current Ip for controlling the pumping in or out of oxygen in the gas sensor 2. Therefore, the sensor control apparatus 3 is not required to have an additional current source for supplying the resistance measurement current to the label resistor 13, whereby the configuration of the sensor control apparatus 3 can be simplified.

In the above-described embodiment, the gas detection system 1 is the sensor control system in the present invention, the label resistor 13 is the characteristic resistor in the present invention, the current DA converter 42 is the energization means in the present invention, the processing of S60 and S90 is the setting means in the present invention, and the AD converter 48 is the voltage measurement means in the present invention.

Second Embodiment

A second embodiment of the present invention will now be described with reference to the drawings. Notably, portions of the second embodiment which differ from those of the first embodiment will be described.

The gas detection system 1 of the second embodiment is identical to the gas detection system 1 of the first embodiment except the point that the label resistor measurement processing is changed.

Here, the steps of the label resistor measurement processing of the second embodiment will be described. This label resistor measurement processing is started immediately after the startup of the sensor control apparatus 3.

Figure 3:
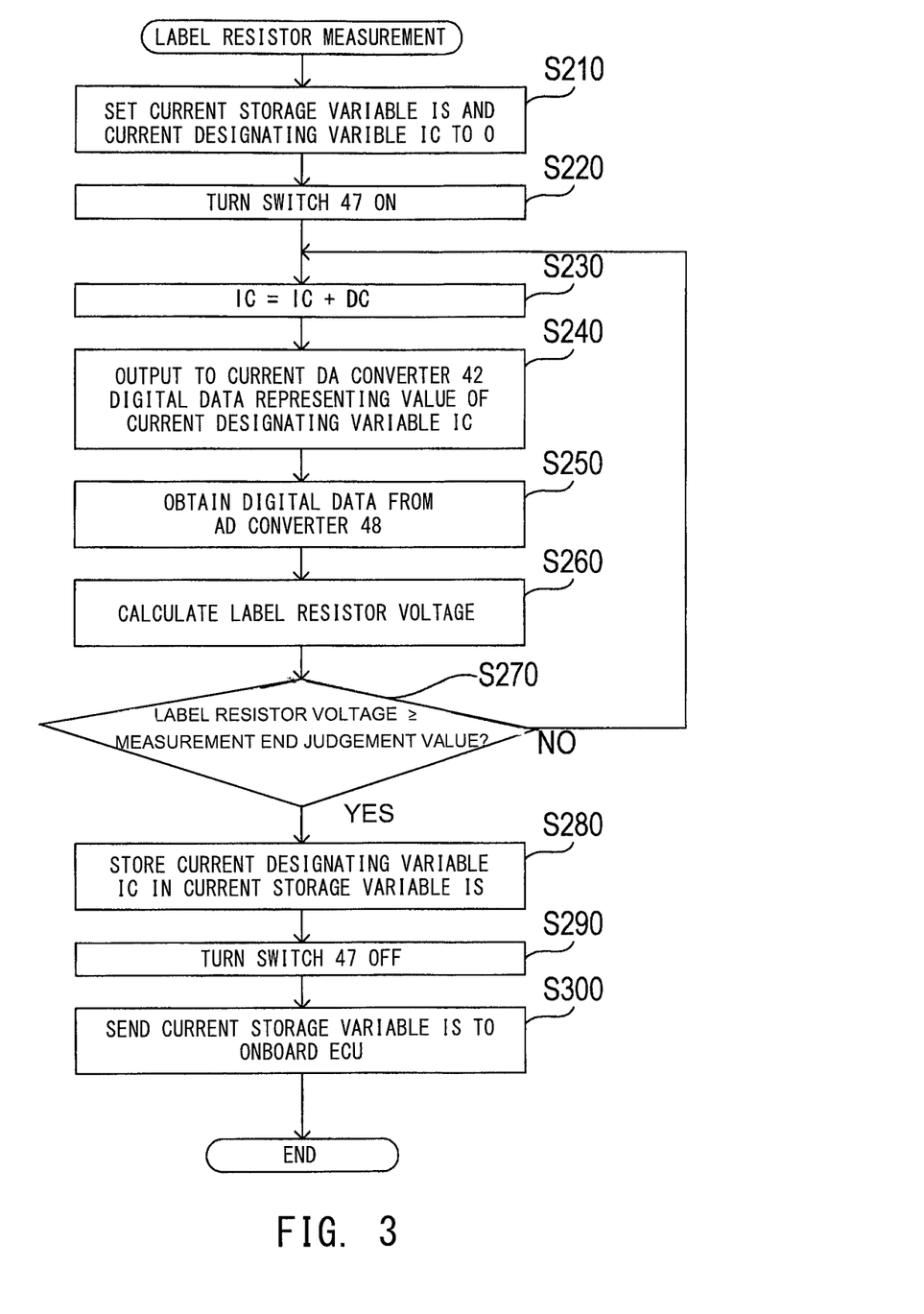
FIG. 3 is a flowchart showing label resistor measurement processing of a second embodiment.

When the label resistor measurement processing of the second embodiment is executed, as shown in FIG. 3, in S210, the CPU 61 of the control section 41 first sets the values of a current storage variable IS and a current designating variable IC provided in the RAM 63 of the control section 41 to 0. Subsequently, in S220, the CPU 61 outputs to the switch 47 a switch state instruction which instructs the switch 47 to enter the on state. As a result, the switch 47 operates to enter the on state.

Further, in S230, the CPU 61 adds a previously set current increase value DC (a value corresponding to 2 μA in the present embodiment) to the value stored in the current designating variable IC and newly stores the resultant value in the current designating variable IC. Namely, the CPU 61 adds the current increase value to the current value designated by the current designating variable IC.

Next, in S240, the CPU 61 outputs to the current DA converter 42 digital data which represent the value stored in the current designating variable IC. As a result, the current DA converter 42 outputs a current having a current value corresponding to the current designating variable IC.

After that, in S250, the CPU 61 obtains digital data representing the voltages of the terminals 50 and 53 from the AD converter 48.

Also, in S260, the CPU 61 calculates the voltages of the terminals 50 and 53 on the basis of the digital data obtained from the AD converter 48, and subtracts the voltage of the terminal 53 from the voltage of the terminal 50 so as to calculate the label resistor voltage.

Subsequently, in S270, the CPU 61 judges whether or not the label resistor voltage is equal to or greater than a measurement end judgment value (0.5 V in the present embodiment) set in advance. In the case where the label resistor voltage is less than the measurement end judgment value (S270: NO), the CPU 61 proceeds to S230 and repeats the above-described processing.

Meanwhile, in the case where the label resistor voltage is equal to or greater than the measurement end judgment value (S270: YES), in S280, the CPU 61 stores in the current storage variable IS the value stored in the current designating variable IC. Subsequently, in S290, the CPU 61 outputs to the switch 47 a switch state instruction which instructs the switch 47 to enter the off state. As a result, the switch 47 operates to enter the off state. Further, in S300, the CPU 61 sends to the onboard ECU digital data which represent the value stored in the current storage variable IS, and ends the label resistor measurement processing.

In the sensor control apparatus 3 configured as described above, the control section 41 sets the designated current value to a plurality of values by increasing the designated current value by a current increasing procedure which is set to increase the designated current value from 0 by the current increase value DC (a value corresponding to 2 μA in the present embodiment) at a time (S210 to S240, S270).

Also, the AD converter 48 measures the label resistor voltage which is the voltage between the opposite ends of the label resistor 13 at the time when the resistance measurement current flows through the label resistor 13. The control section 41 obtains the designated current value at the time when the label resistor voltage measured by the AD converter 48 reaches the measurement end judgment value set in advance (S270, S280).

As a result, the sensor control apparatus 3 can calculate the characteristic resistance on the basis of the value obtained by dividing the measurement end judgment value by the obtained designated current value. In the sensor control apparatus 3, the designated current value used for calculation of the characteristic resistance differs among the ranks set on the basis of the characteristic resistance. Therefore, only one characteristic resistance is contained in each of the characteristic resistance groups into which the characteristic resistances are classified on the basis of the designated current value. Namely, for each of the characteristic resistance groups into which the characteristic resistances are classified on the basis of the designated current value, there exists only one label resistor voltage which falls within the voltage measurement range of the AD converter 48. Accordingly, it is possible to prevent occurrence of a situation in which as the total number of the ranks increases, the voltage difference between ranks adjacent to each other within the voltage measurement range of the AD converter 48 decreases. This is because, in each of the characteristic resistance groups into which the characteristic resistances are classified on the basis of the designated current value, no adjacent rank is present.

As a result, the sensor control apparatus 3 can increase the number of the ranks set in accordance the characteristic of the gas sensor 2, whereby the accuracy in measuring the oxygen concentration through use of the label resistor 13 can be improved.

In the above-described embodiment, the processing of S210 to S240 and S270 is the setting means in the present embodiment, the processing of S270 and S280 is the current value obtainment means in the present invention.

One embodiment of the present invention has been described. However, the present invention is not limited to the above-described embodiment, and can be implemented in various forms without departing from the technical scope of the invention.

For example, in the above-described embodiment, the label resistor is attached to a gas sensor for measuring the concentration of oxygen. However, the present invention can be applied to other types of gas sensors (for example, an NOx sensor) whose characteristics vary among individual sensors.

In the above-described embodiment, the label resistor voltage or the designated current value is sent to the onboard ECU. However, the sensor control apparatus 3 may calculate the resistance of the label resistor 13 on the basis of the label resistor voltage or the designated current value to thereby determine a correction coefficient. Thus, the sensor control apparatus 3 can correct the concentration measured by the gas sensor 2 by using a correction coefficient and send the corrected concentration to the onboard ECU.

In the above-described embodiment, the label resistor voltage or the designated current value is stored in the RAM 63 of the control section 41. However, the label resistor voltage or the designated current value may be stored in an external storage device provided externally of the control section 41 and be sent to the onboard ECU from the external storage device. Moreover, in the above-described embodiment, the designated current value is changed stepwise; however, the designated current value may be changed continuously.

DESCRIPTION OF REFERENCE NUMERALS

1 . . . gas detection system, 2 . . . gas sensor, 3 . . . sensor control apparatus, 11 . . . pump cell, 12 . . . electromotive force cell, 13 . . . label resistor, 41 . . . control section, 42, 43 . . . current DA converter, 44 . . . operational amplifier, 45, 48 . . . AD converter, 46 . . . multiplexer, 47 . . . switch, 61 . . . CPU, 62 . . . ROM, 63 . . . RAM, 64 . . . signal input/output section

The invention claimed is:

1. A sensor control apparatus for controlling a gas sensor which detects a concentration of a particular gas in a mixed exhaust gas, comprising:
   an energization device that supplies a resistance measurement current having a designated current value designated in advance to a characteristic resistor which has a resistance selected from a plurality of previously set resistances so as to represent a characteristic of the gas sensor; and
   a setting device that sets the designated current value to one of two or more values in accordance with a magnitude of the resistance of the characteristic resistor, wherein
   the characteristic resistor is included in the gas sensor and connected to the energization device, and
   the sensor control apparatus is configured to determine the characteristic of the gas sensor based on the resistance of the characteristic resistor.

2. The sensor control apparatus according to claim 1, further comprising a voltage measurement device that measures a resistor voltage which is a voltage between opposite ends of the characteristic resistor at the time when the resistance measurement current flows through the characteristic resistor, wherein
   a first current value and a second current value smaller than the first current value are set as the designated current value, and
   the setting device changes the first current value to the second current value when the resistor voltage is greater than a current changeover judgment value set in advance, said resistor voltage being measured when the resistance measurement current having the first current value is supplied.

3. The sensor control apparatus according to claim 1, further comprising:
   a voltage measurement device that measures a resistor voltage which is a voltage between opposite ends of the characteristic resistor at the time when the resistance measurement current flows through the characteristic resistor; and
   a current value obtainment device that obtains the designated current value when the resistor voltage measured by the voltage measurement device reaches a measurement end judgment value set in advance, wherein
   the setting device sets the designated current value to a plurality of values by increasing the designated current value in accordance with a current increasing procedure set in advance.

4. The sensor control apparatus according to claim 1, further comprising a current source which supplies to the gas sensor an operation control current for controlling operation of the gas sensor, wherein
   the energization device supplies the resistance measurement current to the characteristic resistor by using the current source.

5. A sensor control system comprising:
   a gas sensor which detects a concentration of a particular gas contained in a mixed gas; and
   a sensor control apparatus according to claim 1.

6. The sensor control apparatus according to claim 2, further comprising a current source which supplies to the gas sensor an operation control current for controlling operation of the gas sensor, wherein
   the energization device supplies the resistance measurement current to the characteristic resistor by using the current source.

7. The sensor control apparatus according to claim 3, further comprising a current source which supplies to the gas sensor an operation control current for controlling operation of the gas sensor, wherein
   the energization device supplies the resistance measurement current to the characteristic resistor by using the current source.

8. A sensor control system comprising:
   a gas sensor which detects a concentration of a particular gas contained in mixed a gas; and
   a sensor control apparatus according to claim 2.

9. A sensor control system comprising:
a gas sensor which detects a concentration of a particular gas contained in mixed a gas; and
a sensor control apparatus according to claim 3.

10. A sensor control system comprising:
a gas sensor which detects a concentration of a particular gas contained in mixed a gas; and
a sensor control apparatus according to claim 4.

11. The sensor control apparatus according to claim 1, wherein the characteristic of the gas sensor is a relation between the concentration of the particular gas and a concentration signal output from the gas sensor in accordance with the concentration of the particular gas.

12. A sensor control apparatus for controlling a gas sensor, comprising:
an energization device that supplies a resistance measurement current having a designated current value designated in advance to a characteristic resistor which has a resistance selected from a plurality of previously set resistances so as to represent a characteristic of the gas sensor; and
a setting device that sets the designated current value to one of two or more values in accordance with a magnitude of the resistance of the characteristic resistor, wherein
the gas sensor is configured to detect a concentration of a particular gas in a mixed exhaust gas,
the characteristic resistor is included in the gas sensor and connected to the energization device, and
the sensor control apparatus is configured to determine the characteristic of the gas sensor based on the resistance of the characteristic resistor.

* * * * *